US006346283B1

(12) United States Patent
Hoffman et al.

(10) Patent No.: US 6,346,283 B1
(45) Date of Patent: Feb. 12, 2002

(54) USE OF VALERIANA FOR THE TREATMENT OF RESTLESS LEG SYNDROME AND RELATED DISORDERS

(75) Inventors: Keith Hoffman, Del Mar; Costas Loullis, Carlsbad, both of CA (US)

(73) Assignee: Ancile Pharmaceuticals

( * ) Notice: Subject to any disclaimer, the term of this patent is extended or adjusted under 35 U.S.C. 154(b) by 0 days.

(21) Appl. No.: 09/475,494

(22) Filed: Dec. 30, 1999

Related U.S. Application Data
(60) Provisional application No. 60/126,534, filed on Mar. 26, 1999.

(51) Int. Cl.[7] .................. A61K 35/78; A61K 31/33; A01N 43/00
(52) U.S. Cl. .................. 424/733; 514/183; 514/906
(58) Field of Search .................. 424/195.1, 733; 514/906, 183

(56) References Cited

U.S. PATENT DOCUMENTS 5,763,494 A * 6/1998 Balandrin et al. .......... 514/629

FOREIGN PATENT DOCUMENTS

| EP | WO 97/39355 | 10/1997 |
| EP | WO 98/08498 A | 3/1998 |

OTHER PUBLICATIONS

Boucher, M.A., Restless legs syndrome in home healthcare, *Home Healthcare Nurse*, Aug. 1997, 15(8):551–6.
Dooley, et al., Premipexole, a review of its use in the management of early and advanced Parkinson's disease, *Drugs Aging*, Jun. 1998, 12(6):495–514.
Fox, G.N., Restless legs syndrome, *American Family Physician*, Jan. 1986, 33(1):147–52.
Grandjean, P., Restless legs syndrome—current aspects, *Schweiz Rundsch Med. Prax.*, Apr. 1997, 30:86(18):732–6.
Hornyak, et al., Magnesium therapy for periodic leg movements–related insomnia and restless legs syndrome: an open pilot study; *Sleep*, Aug. 1998, 1:21(5):501–5.
Jones, et al., Restless legs syndrome—a review, *Eur. J. Vasc. Endovasc. Surg.*, Dec. 1997, 14(6):430–2.
Joy, M.S., Clonazepam: benzodiazepine therapy for the restless legs syndrome, *Anna J.* Dec. 1997, 24(6):686–9.
Krueger, B.R., Restless Legs syndrome and periodic movements of sleep, *Mayo Clinic Proc.* Jul. 1990, 65(7):999–1006.
O'Keeffe, S.T., Restless legs syndrome, a review, *Arch. Internal Medicine*, Feb. 1996, 156(3):243–8.
Shannon, et al., Efficacy of pramipexole, a novel dopamine agonist, as monotherapy in mild to moderate Parkinson's disease. The Pramipexole Study Group. *Neurology*, Sep. 1997, 49(3):724–8.
Trenkwalder, et al., Periodic limb movements and restless legs syndrome. *Neurol. Clinic*, Aug. 1996, 14(3):629–50.

Walters, A.S., Toward a better definition of the restless legs syndrome. The International Restless Legs Syndrome Study Group. *Mov. Disord.* Sep. 1995, 10(5):634–42.
Wermuth, L., A double–blind, placebo–controlled, randomized, multi–center study of pramipexole in advanced Parkinson's disease, *Eur. J. Neurol.*, May 1998, 5(3):235–242.
Wetter, et al., Restless legs and periodic leg movements in sleep syndromes, *J. Neurol.*, Apr. 1997, 244(4 Suppl. 1):S37–45.
Williams, D.C., Periodic limb movements of sleep and the restless legs syndrome, *Va. Med. Q.*, Fall 1996, 123(4):260–5.
Morazzoni P., et al., Valeriana offinalis: traditional use and recent evaluation of activity: Fitoterapa, vol. 66, No. 2, 1995, pp. 99–112.
Mennini To, et al.: In vitro study on the interaction of the extracts and pure compounds from valeriana officinalis roots with GABA, Benzodiazepine and Barbiturate receptors in rat brain Fitoterapia, vol. 64, No. 4, 1993, pp. 291–300.
Sanner et al. Deutsche Medizinische Wochenschrift, vol. 122, No. 51–52, pp. 1599–1604, translation enclosed, Dec. 1997.*
PDR for Herbal Medicines, pp. 1204–1207, Jan. 1998.*
Castleman, M. The Healing Herbs, Rodale Press, Emmaus, Pennsylvania, pp. 362–365, 1991.*

* cited by examiner

*Primary Examiner*—Christopher R. Tate
(74) *Attorney, Agent, or Firm*—Knobbe Martens Olson & Bear LLP

(57) ABSTRACT

A novel method of inhibiting at least one symptomology of Restless Legs Syndrome (RLS) and its related disorders, including disorders such as periodic limb movements in sleep (PLMS) and periodic limb movement disorder (PLMD), is disclosed. Said method optionally comprising identifying a host, preferably a human, afflicted with Restless Legs Syndrome (RLS) and its related disorders; and comprising administering to said host a pharmaceutically effective amount of Valeriana, preferably an extract of Valeriana. A novel method of inhibiting at least one symptomology of Restless Legs Syndrome (RLS) and its related disorders is disclosed. The method may also be used to treat a host in order to diminish undesired limb movements, and may involve the administration of a particular compound, found in the above-mentioned extracts, preferably selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid, mimetics thereof, and may involve the administration of a combinations of these particular compounds and mimetics thereof.

19 Claims, 7 Drawing Sheets

DOPAMINE D3 ACTIVE COMPUNDS

10(14)-Aromadendren-40-ol 6,10(14)-Guaiadien-4-ol

| COMPOUND | R GROUP | R' GROUP |
|---|---|---|
| Valerenal | -H | -CHO |
| Valerenol | -H | -CH$_2$OH |
| Valerenic Acid | -H | -CO$_2$H |
| Acetoxyvalerenic Acid | -OAc | -CO$_2$H |
| Hydroxyvalerenic Acid | -OH | -CO$_2$H |

USE OF VALERIANA FOR THE TREATMENT OF RESTLESS LEG SYNDROME AND RELATED DISORDERS

This application claims priority under 35 U.S.C. § 119(e) (1999), from co-pending U.S. Provisional Patent Application Ser. No. 60/126,534, which was filed Mar. 26, 1999.

BACKGROUND OF THE INVENTION

1. Field of the Invention

This invention relates to novel methods for treating Restless Legs Syndrome (RLS) and related disorders, such as periodic limb movements in sleep (PLMS) and periodic limb movement disorder (PLMD), and for diminishing the occurrence of unwanted limb movements. Particularly, this invention relates to the use of Valeriana, and more particularly to an extract of Valeriana officinalis L., for diminishing the occurrence of unwanted limb movements, either associated with or unassociated with RLS and/or related disorders.

2. Description of the Related Art

The set of conditions known as Restless Legs Syndrome (RLS), also known as Ekbom's Syndrome following Ekbom's description of the syndrome in 1944, has been known since at least 1685 (Willis). RLS is a fairly common sensorimotor disorder, yet is not widely recognized by the medical profession or healthcare providers. It is characterized in that it typically gives the individual who suffers from RLS an unpleasant sensation in the legs at rest, causing what is often described as an irresistible desire to move, which generally alleviates the discomfort. (Jones and Deodra, 1997) Also typically, individuals afflicted with RLS experience indescribable crawling sensations in their legs that often occur at night and that are only relieved by moving the legs. (Boucher, 1997) Accordingly, RLS and its related disorders are thought to be a common cause of severe insomnia. (Fox, 1986) RLS is idiopathic in most patients, and has been idenitified as a presenting feature of iron deficiency, and is also common in uremia, pregnancy, diabetes mellitus, rheumatoid arthritis, and polyneuropathy. (O'Keeffe, 1996) PLMD and PLMS, disorders related to RLS, are characterized by episodes of jerking of the limbs, often during periods in which the individual is asleep, and sometimes during periods in which the individual is awake.

RLS affects millions of individuals, having an estimated prevalence of between 1% and 5%. (Wetter and Pollmacher, 1997) Indeed, at least mild symptoms of RLS have been reported to occur in up to 5% of the population of the United States. (O'Keeffe, 1996).

The formal criteria for diagnosis of RLS include: (i) symmetric or asymmetric dysesthesias of the lower, and sometimes also of the upper, extremities; (ii) dysesthesia are typically present at rest, and are especially prevalent at night; (iii) dysesthesia induce a need to move; (iv) movement gives relief, but only for a few seconds. Occasionally, the dysesthesia may be painful. Additional criteria include: (v) involuntary, rhythmic retraction movements occurring especially at night, and especially during sleep stages I and II; (vi) sleep is disrupted and superficial, followed by daytime fatigue. (Grandjean, 1997) Thus, clinical criteria for diagnosis include sleep disturbance, involuntary movements in sleep or wakefulness, a normal neurologic examination, a chronic clinical course, and, in some cases, a positive family history. (Trenkwalder et al., 1996) And the following four minimal criteria for diagnosis have been proposed: (1) desire to move the extremities, often associated with paresthesias/dysesthesias; (2) motor restlessness; (3) worsening of symptoms at rest with at least temporary relief by activity, and (4) worsening of symptoms in the evening or night. (Walters, 1995) The related disorders share some of these characteristics.

The underlying cause of RLS and its related disorders is not clearly known. However, it has been observed that the frequency of occurrence increases with advancing age. In most individuals with RLS, the results of complete blood cell counts and iron, ferritin, folate, and vitamin B12 levels are normal. No hematologic or chemical abnormalities are associated with individuals who experience periodic movements during sleep who also do not have RLS (Krueger, 1990).

Regarding the etiology of RLS and related disorders, pathophysiologically it has been reported that a malfimction of dopamine and opiate receptors in the central nervous system are associated with RLS and related disorders. (Grandjean, 1997) And while the precise aetiology of RLS and PLMS are unknown, it has been reported that periodic leg movements result from a suprasegmental disinhibition of descending inhibitory pathways. An evaluation of the efficacy of certain drugs revealed that, according to one study, the dopaminergic, adrenergic and opiate systems play a major role in the pathogenesis of RLS/PLMS. In spite of this association, therapy of RLS and PLMS remains symptomatic except for some secondary forms. (Wetter and Pollmacher, 1997) Indeed, one study has reported that "[w]hile the Dopamenergic CNS pathways have been thought to be the primary neurotransmitter involved, the opioids secondary, there is mounting evidence that the situation is far more complicated, that many neurotransmitters, including stimulating and inhibiting amino acids, play a part." (Williams, 1996).

Currently, RLS is typically treated by drugs such as clonazepam, narcotics, dopamine agonists, benzodiazipines, clonidine, gabepentin, (Joy, 1997; Wetter and Pollmacher, 1997; Trenkwalder et al., 1996) and magnesium (Hornyak et al., 1998), and typically via oral administration. Currently, one popular pharmaceutical treatment of RLS in the United States is pramipexole, known by the trade name Mirapex, [available from Phannacia and Upjohn] which has been reported to cause major side effects including insomnia, and dizziness. For example: "In pramipexole recipients with early disease, the most commonly experienced adverse events were nausea, dizziness, somnolence, insomnia, constipation, asthenia and hallucinations." (Dooley M, Markham A, Pramipexole. A review of its use in the management of early and advanced Parkinson's disease, Drugs Aging 1998 Jun;12(6):495–514); "The most common adverse events (<10%) were dizziness, insomnia, nausea, and postural hypotension." (Wermuth L, A double-blind, placebo-controlled, randomized, multi-center study of pramipexole in advanced Parkinson's disease, *Eur J Neurol* 1998 May;5(3):235–242); "In the assessment of adverse events, nausea, insomnia, constipation, somnolence, and visual hallucinations occurred more frequently in the pramipexole treatment group compared with placebo patients." (Shannon K M, Bennett J P Jr, Friedman J H, Efficacy of pramipexole, a novel dopamine agonist, as monotherapy in mild to moderate Parkinson's disease. The Pramipexole Study Group. *Neurology* 1997 Sep;49(3):724–8).

Therefore, there exists a need for an effective, alternative treatment and related treatment regime options for individuals who are afflicted with RLS and/or its related disorders. More particularly, there exists a need for treatments that do not induce the unwanted effects observed in modern therapeutics for Restless Legs Syndrome (RLS) and related disorders.

SUMMARY OF THE INVENTION

A novel method of inhibiting at least one symptomology of Restless Legs Syndrome (RLS) and its related disorders is disclosed. Said method comprises identifying a host afflicted with Restless Legs Syndrome (RLS) or a related disorder; and administering to said host a pharmaceutically effective amount of Valeriana. The Valeriana is preferably an extract, and more preferably an extract of Valeriana officinalis L. The host is preferably a mammal, and may also preferably be a canine, feline, or member of the Class Rodentia. The method of the present invention may be used to treat a host in order to diminish undesired limb movements, and may involve the administration of a particular compound, found in the above-mentioned extracts, preferably selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid, and mimetics thereof, and may involve the administration of a combinations of these particular compounds and mimetics thereof.

BRIEF DESCRIPTION OF THE DRAWINGS

The accompanying drawings, which are incorporated in and form part of the specification, merely illustrate embodiments of the present invention. Together with the remainder of the specification, they are meant to serve to explain the principles of the invention to those of skill in the art. In the drawings.

DETAILED DESCRIPTION OF THE PREFERRED EMBODIMENT

Figure 1:
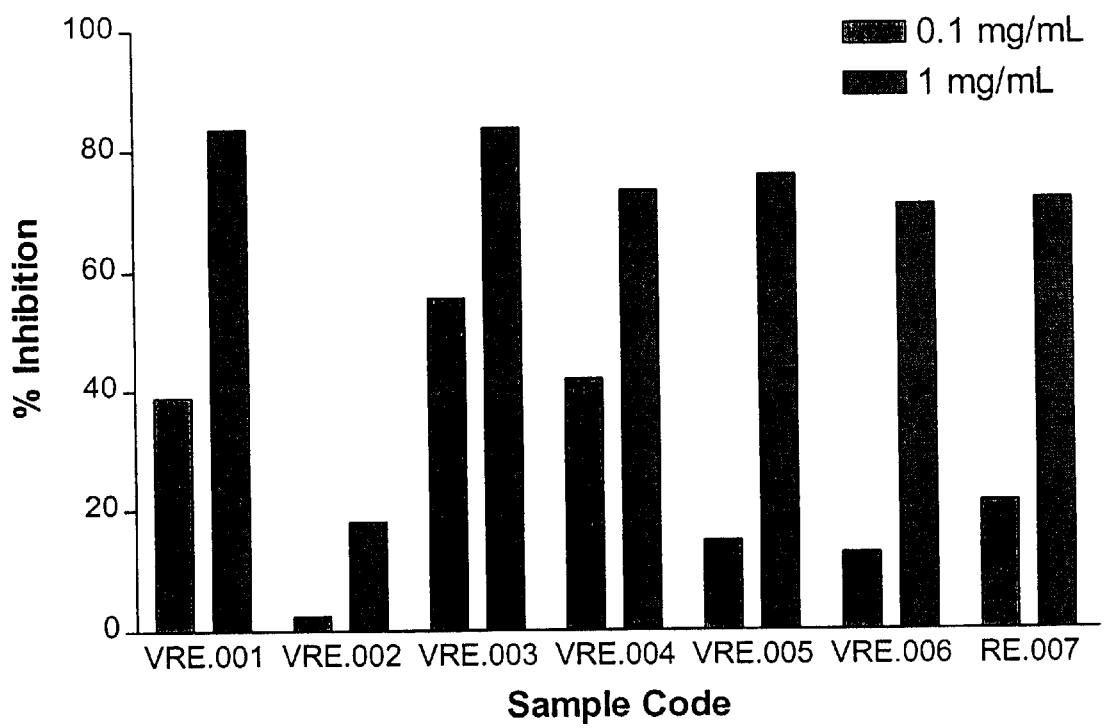
FIG. 1 illustrates a graphic depiction of the effect of commercially available Valerian extracts on binding to the peripheral benzodiazephine receptors according to the invention.

In a preferred embodiment, the present invention provides a natural plant extract, and particularly an extract of Valeriana, and more particularly an extract from Valeriana officinalis L., that affects the peripheral and central nervous system in a manner that alleviates the symptomologies of Restless Legs Syndrome (RLS) and related disorders. Further, the present invention provides the advantage of alleviating the symptomologies of RLS and related disorders without causing the side effects associated with benzodiazipine-type treatment, and other current treatment or treatments of, RLS and related disorders. The present invention provides the advantage of providing an alternative treatment option for RLS and related disorders, of which there is a need in the art.

Another advantage of the present invention, which includes the use of Valerian extract in the treatment of RLS and related disorders, is that extracts of Valeriana have not been shown to cause such side effects and therefore, the treatment of RLS with Valeriana may increase compliance for the RLS patient as well as address the specific problem of insomnia associated with RLS and/or other pharmaceutical treatments for RLS. These current treatments have a wide variety of negative side effects, which have been reported and detailed (Silber, 1997). Also, tolerance to the treatment can develop, causing the efficacy of a particular treatment regime to diminish with time. Also, rebound phenomena are associated with currently known treatments (Krueger, 1990; Hornyak et al., 1998). Additionally, and as would be appreciated by one skilled in the art, current treatments such as benzodiazipines are associated with a host of unwanted effects such as memory loss, addiction potential, and other related side effects.

As used herein, the terms "Valeriana" and "valerian" each refer to any plant of the Valerianaceae, and therefore refers, at least to, the plant designated Valeriana officinalis L. This species includes all recognized subspecies of Valeriana officinalis L. Some of these subspecies are also commonly referred to, in alternative taxonomic systems, as: Valeriana exaltata J. C. Mikan, Valeriana nitida Kreyer, Valeriana palustris Wibel, Valeriana wolgenis Kazak, Valeriana grossheimii Vorosch, Valeriana collina Wallr, Valeriana Rossica P. A. Smirn, Valeriana spryngini P. S. Smirn, Valeriana angustifolia Tausch, Valeriana tenuifolia Vahl, Valeriana wallrothii Kreyer, Valeriana ucrainica Demjan, Valeriana sambucifolia J. C. Mikan, Valeriana excelsa Poir, and Valeriana officinalis L.subsp. excelsa (Poir.) Rouy. Plants of the species Valeriana officinalis L. may be characterized as follows: These plants grow from a short rhizome to 2 m high, flowers, and then die back again in the winter. These plants have pinnately-divided leaves with six to ten pairs of lance-shaped leaflets, and bear many small white or pink flowers in a dense head of several stalked clusters. The heads bare small (5 mm) tapered seeds.

As used herein, the term "root" or "roots" refers to all of subterranean portion of a specifically or generically identified plant, including, but not limited to, the roots, the rhizomes, and the stolons of the specifically or generically identified plant. Where the term "roots" is not modified by a specifically or generically identified plant, it will be understood that the term refers to the roots of the genus, and the various species, of Valeriana.

As used herein the term "Restless Legs Syndrome (RLS) and related disorders" means diseases, disorders, syndromes or conditions characterized by periodic limb movements such as periodic limb movements such as in sleep (PLMS) and periodic limb movement disorder (PLMD), and the treatment of such diseases, disorders, syndromes or conditions includes any pharmacological means of diminishing the occurrence of unwanted limb movements.

As used herein, the terms "reduces," "reduced," or "reducing," when used to refer to one or more symptomology of a disease, refers to any observable lessening of that characteristic when the method or composition of the present invention is compared to prior art methods or compositions.

As used herein, the terms "disorder" and "disease" refer to any disorder, disease, condition, syndrome or combination of manifestations or symptoms recognized or diagnosed as a disorder. If modified by reference to a particular disease or by reference one or more or a set of manifestations or symptoms, that usage of "disorder" or "disease" refers to any such disorder, disease, condition, syndrome or combination of such manifestations or symptoms recognized or diagnosed as a such disorder.

As used herein, the term "pharmaceutically effective amount" refers to an amount sufficient to alleviate, in any degree or manner, one or more of the manifestations or symptoms recognized or diagnosed as associated with the modifying disorder, the modifying manifestations, or the modifying symptom.

EXAMPLE 1

Effects of Valerian Extract on Peripheral and Central Nervous System

In Table 1, data are shown which demonstrate that an extract from Valeriana officinalis L. affected the peripheral and central nervous system in a manner consistent with alleviating one or more of the symptomologies of Restless Legs Syndrome (RLS) and related disorders. All bio-assays, except the Rat A1, were performed at the following laboratory according to standard methods known to those skilled in the art:

Panlabs Taiwan, Ltd.
158 Li-Teh Road, Peitou
Taipei, Taiwan
R.O.C.

Two examples of suitable assay procedures are as follows:
Human D3 Assay:

This assay measures binding of [$^3$H]-Spiperone to human dopamine D3 receptors. CHO cells stably transfected with a plasmid encoding the human dopamine D3 receptor were used to prepare membranes in modified Tris-HCl pH 7.4 buffer using standard techniques. A 10 mg aliquot of membrane was incubated with 2 nM [$^3$H]-Spiperone for 120 minutes at 37° C. Non-specific binding was estimated in the presence of 25 $\mu$M S-(–)-sulpiride. Membranes were filtered and washed three times and the filters are counted to determine the amount of [$^3$H]-Spiperone specifically bound. Compounds were screened at 10 $\mu$M.

Human A1 Assay:

This assay measures binding of [$^3$H]-DPCPX to adenosine A1 receptors. CHO cells stably transfected with a plasmid encoding the human adenosine A1 receptor were used to prepare membranes in modified HEPES pH 7.4 using standard techniques. A 10 mg aliquot of membrane was incubated with 1 nM [$^3$H]-DPCPX for 90 minutes at 25° C. Non-specific binding was estimated in the presence of 100 $\mu$M R(–)-PIA. Membranes were filtered and washed three times and the filters were counted to determine [$^3$H]-DPCPX specifically bound. Compounds were screened at 10 $\mu$M.

Rat adenosine A1 receptor binding assays were performed at the following laboratory according to standard methods known to those skilled in the art:

Oceanix Biosciences
7170 Standard Drive
Hanover, Md. 21076

Rat A1 Assay:

This assay measures binding of [$^3$H]-8-Cyclopentyl-1,3-dipropylxanthine to adenosine A1 receptors. Rat cortical membranes, prepared using standard techniques, were used as a source of the receptor. Reactions were carried out in 50 mM TRIS-HCl (pH 7.7) for 60 minutes at 25° C. Non-specific binding was estimated in the presence of 10 $\mu$M 2-chloroadenosine. The reaction was terminated by rapid vacuum filtration onto glass fiber filters. Radioactivity trapped onto the filters was determined and compared to control values in order to ascertain any interactions of test compound with the adenosine A1 binding site.

Figure 2:
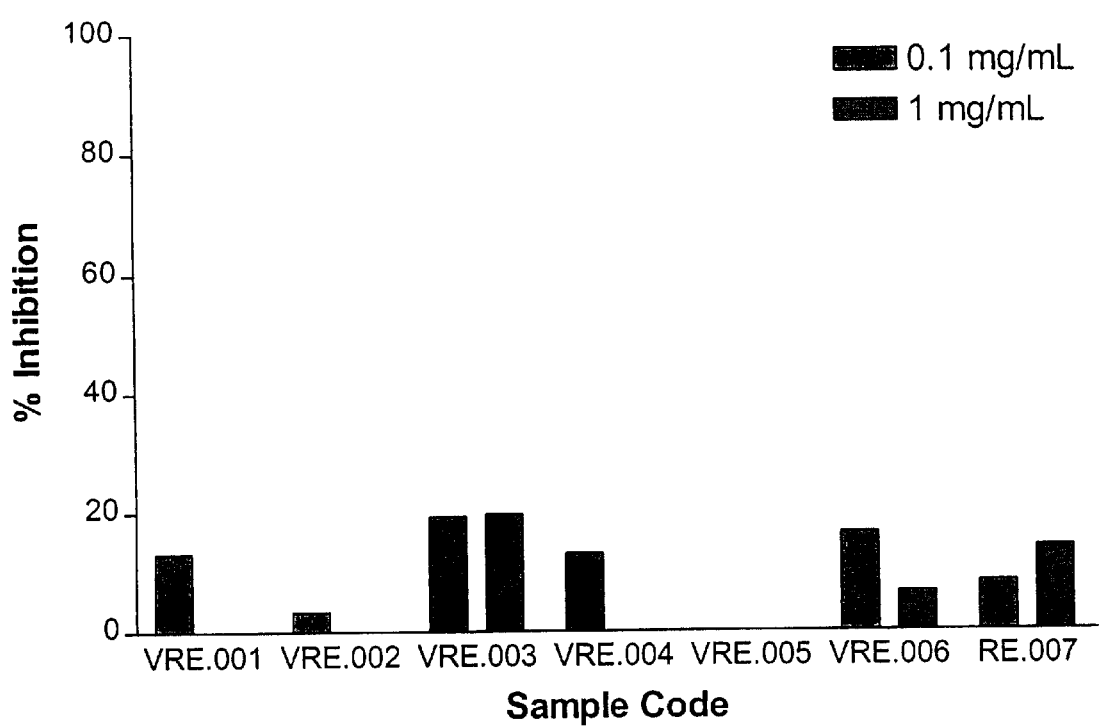
FIG. 2 illustrates a graphic depiction of the lack of effect of commercially available Valerian extracts on binding to the central benzodiazephine receptors according to the invention.

It has further been demonstrated, through in vitro binding tests, that extracts of Valeriana officinalis L., produced substantially according to the method described herein, favorably interact with certain Central Nervous System (CNS) receptors, for example, the GABA, Adenosine, and Dopamine receptors. Such bind would explain the calming action of said extracts (see Table 1). In contrast, the CNS binding site associated with benzodiazepines was not affected by said Valeran extracts (see FIGS. 1 and 2). The results depicted in FIG. 2 indicate, via an in vitro model, that extracts of Valeriana officinalis L. will not result in the problematic side effects and side effect profiles associated with currently available benzodiazepine-type drugs. Additionally, as demonstrated by the data depicted in FIG. 1, extracts of Valeriana officinalis affect the binding of peripheral benzodiazepine receptors. Thus, is it believed, although the invention is not limited by any theory or hypothesis, that the peripheral benzodiazepine receptors mediate the activity of mitochondria in muscle cells, ad thereby effect muscle activity (see FIGS. 1 and 2), and therefore mediate muscle calming.

TABLE 1

Percent Inhibition of Various Extract Fractions Against Various Receptors

| | % Inhibition | | | | | | | |
|---|---|---|---|---|---|---|---|---|
| | VRE.001 | VRE.002 | VRE.003 | VRE.004 | VRE.005 | VRE.006 | RE.007 | Mean | SD |
| A1 Human | | | | | | | | | |
| 0.1 mg/mL | −10 | −9 | 17 | 14 | −12 | −9 | 8 | −0.14 | 12.62 |
| 1 mg/mL | 38 | −9 | 60 | 47 | 28 | 32 | 23 | 31.29 | 21.68 |
| A1 Rat | | | | | | | | | |
| 0.1 mg/mL | 43.85 | 12.64 | 11.36 | 28.45 | 21.86 | 20.57 | 22.76 | 23.07 | 10.91 |
| 1 mg/mL | 84.69 | −7.28 | 47.93 | 76.01 | 60.56 | 42.77 | 52.81 | 51.07 | 29.80 |
| BDZ Central | | | | | | | | | |
| 0.1 mg/mL | 13.08 | 3.32 | 19.23 | 13.01 | −1.9 | 16.4 | 8.26 | 10.20 | 7.46 |
| 1 mg/mL | −42.73 | −11.31 | 19.61 | −31.61 | −13.73 | 6.57 | 13.98 | −8.46 | 23.32 |
| BDZ Peri | | | | | | | | | |
| 0.1 mg/mL | 38.83 | 2.32 | 55.5 | 41.86 | 14.66 | 12.63 | 21.19 | 26.71 | 19.04 |
| 1 mg/mL | 83.64 | 17.82 | 83.85 | 73.33 | 75.71 | 70.84 | 71.73 | 68.13 | 22.82 |

TABLE 1-continued

Percent Inhibition of Various Extract Fractions Against Various Receptors

| | % Inhibition | | | | | | | | |
|---|---|---|---|---|---|---|---|---|---|
| | VRE.001 | VRE.002 | VRE.003 | VRE.004 | VRE.005 | VRE.006 | RE.007 | Mean | SD |
| CI Channel | | | | | | | | | |
| 0.1 mg/mL | 12.58 | −33.05 | 11.7 | 3.81 | 1.79 | 9.45 | −6.09 | 0.03 | 15.98 |
| 1 mg/mL | 98.15 | 14.66 | 40.02 | 86.72 | 91.95 | 49.34 | 10.46 | 55.90 | 36.73 |
| D1 | | | | | | | | | |
| 0.1 mg/mL | 13.52 | 24.52 | 43 | 8.95 | 5.36 | 37.64 | 14.48 | 21.07 | 14.50 |
| 1 mg/mL | 70.25 | 34.88 | 37.78 | 36.55 | 68.16 | 49.22 | 23.44 | 45.75 | 17.69 |
| GABA-A | | | | | | | | | |
| 0.1 mg/mL | 94.5 | 61.56 | 83.24 | 91.89 | 90.49 | 89.53 | 36.16 | 78.20 | 21.61 |
| 1 mg/mL | 93.24 | 95.62 | 97.56 | 91.37 | 100.13 | 96.79 | 59.73 | 90.63 | 13.92 |
| GABA-B | | | | | | | | | |
| 0.01 mg/mL | 26 | 13 | −10 | 46 | 12 | 7 | −6 | 12.57 | 19.08 |
| 0.1 mg/mL | 82 | 14 | 28 | 66 | 77 | 53 | 4 | 46.29 | 31.14 |
| 1 mg/mL | 102 | 96 | 81 | 116 | 105 | 110 | 48 | 94.00 | 23.14 |

EXAMPLE 2

Process for Preparing a Valerian Extract

As a further non-limiting, preferred example, an extract of the plant Valeriana officinalis and specifically, of its roots, wherein the amount of valeoptriates in the extract is reduced below a detectable level, may be obtained, in a manner substantially consistent with that described herein, by performing the following steps, in the following sequence. As will be appreciated by those of skill in the art, such a process yields aan extract possessing the following compounds as constituents: 10(14)-Aromadendren-4-ol, 6,10(14)-Guaiadien-4-ol, Valerinal, Valerenol, Valerenic acid, Acetoxyvalerenic acid, Hydroxyvalerenic acid. Additionally, mimetics of these constituents will possess certain similar biological properties as the identified constituents, and combinations of these constituents, including combination of these constituents and mimetics thereof, may be employed within the meaning of the present invention.

In producing an extract of the plant Valeriana officinalis and specifically, of its roots, by performing the following steps, it will be appreciated that, of the plants of the Valerienaceae family, only V. officinalis L. is known to contain extractable valerenic acid in its roots. Furthermore, extracts of V. officinalis L. roots exhibit sedative and anxiolytic action. Accordingly, it is important to verify that the particular roots to be extracted are roots of the species V. officinalis L. and not of another plant, or more specifically of another member of the Valerianaceae family. This is particularly true because many of the plants in this family are phenotypically similar and are therefore capable of being substituted for an another. Thus, a preferable means to identify V. officinalis L. is to identify valerenic acid directly in the exctract.

The extraction process of the present invention, unlike known methods of extracting V. officinalis L. roots from water, yields a measurable amount of valerenic acid. The extraction of V. officinalis L. roots in water does not yield isolatable valerenic acid. Accordingly, the present extraction method is preferable to, and provides benefits not obtainable throught the use of knnown water-based extraction methods. For example, the present process allows for the extraction of a pharmaceutically-effective composition that can be independently verified as being from the roots of V. officinalis L., rather than from the roots of another plant or of a phenotypically-similar member of the Valerienaceae family.

Another aspect of the extraction method of the present invention that is superior to known valerian extraction method concerns the in-process reduction of the content of valepotriates in the extracts. While it is true that valepotriates may contribute to the pharmaceutical activity of valerian extracts, valepotriates are also potentially dangerous. For example, valepotriates have been shown to be cytotixic in vitro, and exhibit potential mutagenic activity. [Von der Hude W., Scheutwinkel-Reich M., Braun R., and Dittmar W. "In vitro mutagencity of valepotriates" Arch Toxicol 56 (1985) 267–71; Von der Hude W., Scheutwinkel-Reich M., and Braun R. "Bacterial mutagenicity of the tranquilizing constituents of Valerianaceae roots." Mutat Res 169 (1986) 23-7] Also, orally-administered valepotriates reach the brain and other organs in vivo, and have been shown to be capable of irreversibly alkylating DNA and proteins. [Wagner, H. and Juric, K, Planta Med. (1980) 38:366–376] According, it is desirable to eliminate, or to at least substantially reduce the level of valepotriates in valerian extracts. The extraction method of the present invention achieves this objective, while simultaneously achieving the objective of extracting a measurable quantity of valerenic acid as described above.

As used herein, the term "valerian" refers to any plant of the Valerienaceae family possessing extractable valerenic acid in its roots, and therefor refers, at least to, the plant designated Valeriena officinalis L. or alternatively herein, V offifinalis L. This species includes all recognized subspecies of Valeriana officinalis L. Some of these subspecies are also commonly referred to, in alternative taxonomic systems, as: Valeriana exaltata J. C. Mikan Valeriana nitida Kreyer, Valeriana palustris Wibel, Valeriana wolgenis Kazak, Valeriana grossheimii Vorosch, Valeriana collina Wallr, Valeriana Rossica P. A. Smirn, Valeriana spryngini P. S. Smiorn, Valeriana angustifolia Tauch, Valeriana tenuifolia Vahl, Valeriana wallrothii Kreyer, Valeriana ucrainica Demjan, Valeriana sambufifolia J. C. Mikan, Valeriana excelsa Poir, and Valeriana officinalis L.Subsp. excelsa (Poir.) Rouy. Plants of the species Valeriana officinalis L. may be characterized as follows: These plant grows from a short rhizome to 2 m high, flowers, and then dies back again in the winter.

These plant has pinnately-divided leaves with six to ten pairs of lance-shaped leaflets, and bears many small white or pink flowers in a dense head of several stalked clusters. These heads bare small (5 mm) tapered seeds.

As used herein, the term "valerian extracts" most generally refers to the composition isolatede from the roots of plants of the Valerianaceae family according to a specified extraction procedure, and preferably refers to the composition isolated from the roots of valerian or Valeriana officinalis L. according to a specified extraction procedure. These extracts comprise essential oils, valerenic acids, valepotriates (iridoids), kessane derivative, valeranon, valerenal, fatty acids, carbohydrates and certain amino acids.

As used herein, the term "valerinic acids" refers to all chamically stable derivatives of valerinic acid. In its most limited, and preferable, connotation, this term refers to valerenic acid, acetoxyvalerinic acid, and dydroxyvalerinic acid (these three compounds, in aggregate, are also referred to herein a "VAs"). These compounds, either individually, in the aggregate, or based on their respective ratios, may be used as standards to evaluate the extract processes herein described and/or to evaluate the plant from which the extracted roots have been obtained. Valerenmic acid, in particular, may be used to verify that the roots exxtracted are of the species Valeriana officinalis L.

Valerenic Acid (also referred to herein as "VA") is represented by the formula $C_{15}H_{22}O_2$, has a molecular weight of 243.33 amu, a UV $\lambda_{max}$ at 218 mm with a log $\epsilon$ of 4.232, and an $[\alpha]^{20}_D$ of –117.8° (c=1.64, EtOH). Acetoxyvalerenic acid (also referred to herein as "AVA") is represented by the formula $C_{17}H_{24}O_4$, has a molecular weight of 293.35 amu, a UV $\lambda_{max}$ at 217 nm with a log $\epsilon$ of 4.184, and has an $[\alpha]^{20}_D$ of –36.7° (c=1.15, EtOH). Hydroxyvalerenic acid (also referred to herein as "HVA") is represented by the formula $C_{15}H_{22}O_3$, has a molecular weight of 250.34 amu, a UV $\lambda_{max}$ at 212 nm with a log $\epsilon$ of 4.305, and has an $[\alpha]^{20}_D$ of –98.4° (c=0.63, EtOH). Accordingly, UV measurements at 220 nm may be used to determine the content of the valerenic acids in a given sample or aliquot.

As used herein, the term "valepotriates" (these compounds, in aggregate, are also referred to herein as "VPs") refers to all chemically unstable, thermolabile triesters of polyalcohols having an iridoid structure that may be found in the roots of members of the Valerianaceae family. The most typical calepotriates, as that term is used herein, are the diene-type valepotriates, valtrate, acevaltrate, and isovaltrate. The decomposition products of valepotriates, for example, baldrinal and homobaldrinal are not within the definition of "valepotriates," but may be referred to as "valeportriate derivatives" or "valepotriate decomposition products." UV measurements at 200, 254, and 320 nm are preferably used to determine the content of valepotriates in a given sample or aliquot.

As used herein, the term "isolated" refers to the state of being free of other, dissimilar compounds with which the extracted components of the invention will normally be associated in their natural state, so that upon being "isolated" the pharmaceutically-active components comprises at least 0.5%, 1%, 2%, 4%, 5%, 10%, 20%, 50%, and most preferably at least 75% of the mass, by weight, of a given sample.

As used herein, the term "water" refers to water, and preferably to potable water, which term includes purified and/or de-ionized water. Water, as used herein, may have dissolved within it a significant amount of any water-soluble solute, such as a salt or a sugar.

As used herein, the term "alcoholic" refers to a process of or an extract obtained from extraction in an alcoholic extraction solvent containing a significant percentage of alcohol. "Alcoholic extraction solvent" refers to extraction solvent havibng greater than approximately 10% alcohol by volume, and preferably refers to extraction solvents having at least approximately 25%, 30%, 35%, 40%, 45%, or preferably 50% alcohol by volume. Most preferably, "alcoholic extraction solvent" refers to an extraction solvent that are 100% alcohol. Preferable, "alcoholic extraction solvent" refers to any $C_1$–$C_6$ alcohol, for example, methonal, ethanol, butanol or propanol, or any combination thereof, and most preferably refers to denatured ethanol (approximately 95% ethanol and approximately 5% methanol). The term "ethanol" shouldl be understood as referring to denatured alcohol unless specifically identified otherwise.

As used herein, the term "roots" refers to all of subterranean portion of a specifically or generically identified plant, including, but not limited to, ther roots, the rhizomes, and the stolons of the specifically or generically identified plant. Where the term "roots" is not modified by a specifically or generically identified plant, it will be understood that the term refers to the roots of the species, and subspecies of, Valeriana officinalis L.

The extraction process of the present invention most generally involves heating a mixture if the roots and an alcoholic extraction solvent for an extended period of time to obtain valerenic acid and valerenic acid derivatives in the exctract, and to signficantly reduce the amount of valepotriates in the extract. This process, whcn compared to currently known processes, sigificantly reduces the amount of valepotriates in the valerian extract, while maximizing the amount of valerenic acid and of valerenic acid derivitives. It is contemplated that the extract, isolated according to the method of the present invention, may ultimately be used for a pharmaceutically active formulation.

The process includes an extraction process. The process for preparing such a formulation is described to place the extraction process in the context of the preparation of the pharmaceutically active formulation. The following five steps comprise the process for preparing such a formulation: Pre-Extraction Processing of the Root, Extraction, Drying and Milling of the Drug Substance, and Formulation of a Tablet or Capsule. Additional or alternative steps, as well as the use of different pharmaceutical formulations, may be added without departing from this process.

Pre-Extract Processing of the Root. The roots may be prepared for extraction by grinding, chipping, or pulverizing to a powder in a hammermill, or like a instrument, as will be appreciated by those of skill in the art. After such pre-extraction processing, preferably at least 70%, 75%, or 80%, and most preferably 85% or 90of the mass of the roots pass through a Tyler 20-mesh screen. Also preferably, the raw or processed roots are stored in a durable non-reactive, preferably plastic, and more preferably polyethylene, container or containers. These containers may be doubly-lined with bags of like material and closed or closeable with a lid composed of like material.

Extraction. The valerian root, whether, as prferred, processed as decscribed above or in an unprocessed state, may be added to an extraction solvent. Most preferably, the root is added in a ratio of approximately one kilogram to approximately five liters of extraction solution. The extraction solvent preferably is an alcoholic extraction solution, comprising between approximately 30% to approximately 100% (volume/volume; v/v), alcohol and between approximately 70% (volume/volume; v/v) to 0% (v/v) water. Preferably, the alcoholic extraction solvent comprises approximately 50% to approximately 100% (v/v), approximately 55% to approximately 95% (v/v), approximately 65% to approximately 85% (v/v), and approximately 65% to approximately 75% (v/v) alcohol. Specifically, the alcoholic extraction solvent may comprise approximately 50% (v/v), approximately 60% (v/v), approximately 70% (v/v), approximately 80% (v/v, approximately 90% (v/v) alcohol and approximately 100% alcohol. The alcohol used in th alcoholic extraction solvent is fully miscible in water, and is preferably denatured ethanol (95% ethanol+5% methanol), but may be any $C_1$–$C_6$ alcohol, including but not limited to methanol, ethanol, n-butanol isobutanol, n-propyl alcohol, and isopropyl alcohol.

The mixture of root and alcoholic extraction solvent may be stirred by any mechanical device conventionally known for such purpose, including but not limited to an overhead stirrer, a magnetic stirrer assembly, and/or a built-in stirrer, and may be suitable for or adapted to the particular extraction vessel employed. The mixture may be heated to between approxiately 65° C. and 85° C., and more preferably between approximately 70° C. and 80° C., or alternatively, the temperature of reflux. Specifically, the mixture may be heated to 50°, 55°, 60°, 65°, 70°, 75°, 77°, or 80° or reflux. Various conventional methods may be used to heat the mixture, including but not limited to heating mantels or other resistive heating coils.

Preferably, the mixture is heated to any of the above-described temperature for at least one, one and one-half, two, two and one-half, three, three and one-half hours, four, or up to five hours. These durations, most preferably the latter three durations, are selection to sigificantly reduce the level of valepotriates relative to the initial value, preferably at least a 50% reduction. (Final Value/Initial Value=Percent Reduction). More preferably the reduction is by 60%, 70%, 75%, 80%, 90%, 95%, and most preferably 100% of the detectable level of valepotriates. In the latter case, the valepotriate level is not dectectable by conventional techniques. The final valepotiate level may be obtained and may also be compared to that found in commercial valerian extracts.

Optionally, the mixture may then be cooled, preferably to room temperature or altenatively to a temperature above room temperature, including 30° C., 35° C., 40° C., 45° C., and 50° C. The solids may then be separated from the liquid (by ffiltration or centrifugation or any other conventioinal method for separation). The extraction vessel and the separated solids may be rinsed with the extraction solvent, described above. For such a rinse, from approximately four liters, three liters, two liters, or preferably one liter of of extraction solvent may be used for each kilogram of root initially extracted.

Also optionally, the filtrate containing the extracted material may be concentrated to an oily consistency under reduced pressure, including appoximatly 0.9, 0.8, 0.7, 0.6, and 0.5 atms, at a temperature above room temperature, including 30° C., 35° C., 40° C., 45° C., and 50° C. Optimally, a final volume of approximately 0.15 liters for each kilogram of root extracted is obtained.

Addition of Excipient to facilitate drying. The concentrate may be mixed with an excipient to facilitate drying. The excipient may be chosen from any commercially-available excipient or mixtures thereof, but is preferably selected from the following: Maltodextrin, NF, Tricalcium Phosphate, and Silicon Dioxide or other conventional excipient and any combination or mixture threof as will be recognized by those of skill in the art. After addition of the excipient, the excipient will preferably comprise between approximately 10% and 40%, and more preferably between 20% and 25%, of the drug substance.

Drying and Milling of the Drug Substance. The concentrated valerian extract and excipient, if added, is dried under reduced pressure, including approximately 0.9, 0.8, 0.7, 0.6, and 0.5 atms, at a slightly above room temperature, including 30° C., 35° C., 40° C., 45° C., and 50° C. Optimally, the drying is continuous until water content is equal to or less than less than 15%, 10%, or 5%, as measured by Karl Fischer analysis. The dried ae may then be milled to a target of 80%, 85%, 90%, or 95% by weight passing through a size-exclusion screen of 60-mesh, 70-mesh, 80-mesh, 90-mesh, or 100-mesh.

Optionally drying of the extract may be accomplished by spray drying or any other conventional drying method as will be understood by one of ordinary skill in the art.

Certain of the constituents of V. officinalis L have been identified a sesquiterpenes (in the volatile oils) and iridoids (known as valepotiates). The total content of volatile oil vaies widely vithin a single species, and also may vary between different species. The oil typically consists of mixtures of monoteropene and sesquiterpene derivatives. The amount of valepotriates also varies. The process of the present invention has been shown to reduce the amount of valepotriates when compared to currently practiced valerian extraction processes.

When verfying the plant source and process of the extracion process of the present invention, valerenic acid, acetoxyvalerenic acid, and hydroxyvaleremnic acid are preferably used as marker compounds for analysis of the extract and later formulations based on the extracts. The process of the present invention significantly reduces the amount of valepotriate, while optimizing the yield of valerenic acid, acetoxyvalerenic acid, and hydroxyvaleric acid either alone or in the agegate. Active constituents of the extract of the present invention include, but are no limited to, valerenic acid and its derivatives (for example, acetoxyvalerenic acid and hydroxyvalerenic acid), kessane derivatives, valeranone, valerenal, small chain carboxylic acids, fatty acids and amino acids; the extract may also contains sugars, and trace amounts of other aliphatic acids, alkaloids, phenolic acids, flavonoids, free fatty acids, sugars, and salts.

The present invention is herein described in detail through a variety of examples. It will be understood by those skilled in the art that the invention is not limited to the specific examples provided herein. Furthermore although various amounts of plant material, specifically, V. officnalis L roots, and vaious other parameters under which extractions are performed, including specific pH conditions, temperatures, durations, and extraction solvents, are specified in the following examples, it will be understood by those skilled in the art that the invention is not limited to these specific plants, and these specific amounts and/or parameters. It will also be understood by those skilled in the art that the amount or type of plant material, the pH, temperature, solvent, and/or duration of extraction may be varied, and that the resultant process will still achieve one or more of the objectives of the invention.

(1) At an extraction facility the Valeriana officinalis L. rhizome, roots, and stolons (Valerian biomass) are prepared for extraction by chipping in a hammermill with an appropriate screen installed for sizing. The chipped Valerian biomass is analyzed to ensure that at least 85% passes through a Tyler 20-mesh screen. The chipped Valerian biomass is packaged in a polyethylene container, doubly lined with polyethylene bags, and closed with a polyethylene lid.

(2) The chipped Valerian biomass is added to an extraction solvent in a ratio of 1 kg of chipped Valerian biomass to 5 L of extraction solvent, then stirred. The extraction solvent consists of a mixture of 70% denatured ethanol (95% ethanol+5% methanol) and 30% potable water by volume. The mixture is stirred and heated to reflux (77–80° C.) for at least 5, or approximately 6, 7, 8, or 10 hours to reduce the levels of valepotriates by a target of not less than 95% from the level initially found in the extraction mixture, and to a low as undetectable levels. The mixture is cooled below reflux (approximately 40–50° C., or more particularly 42, 45, and 47° C.) and the solids are filtered from the liquid. The extraction vessel and the solids in the filter are rinsed with the same solvent solution as used for extraction. The rinse consists of 2 L of solvent solution for each 1 kg of chipped Valerian biomass extracted. The filtrate containing the extracted material is concentrated to an oily consistency under reduced pressure at approximately 50° C., or approximately 45° C. or 55° C., to a final volume of approximately 0.1 6 L for each 1 kg of chipped Valerian root extracted.

(3) Optionally, the concentrate is mixed wih an acceptable chemical base to reduce the odor of the extract. Specifically, the extract may be mixed with a chemical base, wherein the base is present in an amount sufficient to deodorize the extract. The chemical base may be any of the commonly-known or used bases, such as calcium carbonate, sodium carbonate, sodium bicarbonate, calcium hydroxide, aluminum hydroxide, magnesium hydroxide, sodium hydroxide, potassimn hydroxide, or any other chemical based sufficient amount of a chemical base to eliminate the odor, and is preferably is non-toxic. Contrary to the teachings of the prior art, which teaches that valepotriates and the degradation products of valepotriates are the odor-causing agents of extracts of Valerian root, isovaleric acids, and like acid components (such as the butonic, pentanoic and hexanoic acids) of Valerian root, have been identified as the odor-causing agents. An extract of Valerian root may also be made to have a reduced odor by the step of combining the extract, or mixing the extract, with the commercially-available antacid Maalox®, or by combining the extract with calcium carbonate. Specified amounts of extract of Valerian root, 250, 500, 1000 mg, may be combined with 1000 mg of calcium carbonate.

(4) The concentrate is mixed with an excipient (maltodextrin) to facilitate drying. The final maltodextrin concentration by weight will be between 20–25% of the botanical drug substance.

(5) The mixture of concentrate and excipient is dried under a reduced pressure of 28–30 inches Hg, gauge, and a temperature of 40–50° C., or more particularly 42, 45, and 47° C., until the water content is 5% or less, or 10% or less, or 2.5% or less, by Karl Fisher analysis. The dried extract on excipient is milled to a target of 90% passing through an 80-mesh screen.

(6) The final powder is packaged in 60 L capacity containers constructed of High Density Polyethylene (HDPE). The containers are double lined with Low Density Polyethylene (LDPE) bags that contain no dye and are extruded from virgin polymer only. Twisting the excess bag closed at the open end and securing it with an elastic band closes each bag within the packaging container. These containers have a HDPE lid with a gasket seal to the container. The lid is secured to the container with an aluminum clamp band. The clamp band is secured with a non-removable security seal.

Said extract, or other extracts of Valeriana, obtained via methods that are appreciated by those skilled in the art, are administered to a host, said host having been identified as afflicted with Restless Legs Syndrome and related disorders, in a pharmaceutically effective amount.

Furthermore, said extract, or other extracts of Valeriana, obtained via the above-described method may be, as will be appreciated by those skilled in the art, administered to a host, preferably a mammalian host, and most preferably a canine, a feline, a rodent, (include a murine), or a human host, said host having been identified as suffering from or afflicted with undesired limb movements associated with Restless Legs Syndrome (RLS) or a related disorder. As will be appreciated by those of skill in the art, the above-described extract is preferably delivered in a pharmaceutically effective amount that does not induce unwanted side effects.

The extract produced, and preferably the tablets produced according to the methods of the present invention advantageously may be administered to an individual in a dose containing a pharmaceutically-effective amount of Valerian, Valerian extract, or component(s) therein. This administration can be through any effective route. It is contemplated that administration may be effected, for example, preferably orally, but also may also be administered intramuscularly, subcutaneously, intraperitoneally, transdermally, transmucosally, buccally, or through inhalation or pulmonary infusion. Dosages that are contemplated for a 70 kg adult human range from a lower limit of 10, 25, 50, 100, 150, 200, or 250 mg to an upper limit of 750, 1000, 1500, 2000, 2500, 3000, 4000, 5000, or up to 10,000 mg. of the compositions described herein, or other extracts of valerian. Preferred dosages for a 70 kg human are from about 100, 200, or 250 mg to about 1000, 1500, 2000, or 2500 mg. These dosages can be administered once, twice or up to four times per day, or two or more dosages may be combined. The dose may also be tailored to achieve a desired effect, but will depend on such factors as weight, diet, concurrent medication and other factors which those skilled in the medical arts will recognize.

The present invention also encompasses pharmaceutical compositions comprising a pharmaceutically acceptable carrier prepared for storage and subsequent administration, which have a pharmaceutically effective amount of the extract disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

These compositions may be formulated and used as, preferably, tablets, and also as capsules for oral administration. Suitable additional excipients are, for example, water, saline, dextrose, mannitol, lactose, lecithin, albumin, sodium glutamate, cysteine hydrochloride, and the like. In addition, if desired, the pharmaceutical compositions may contain relatively small amounts of nontoxic auxiliary substances, such as wetting agents, pH buffering agents, and the like.

In practicing the compositions of the invention, the formulated dosage may be used alone or in combination with other therapeutic or diagnostic agents. These products can be utilized in vivo, ordinarily in a mammal, preferably in a human, or in vitro. In employing them in vivo, the products or compositions can be administered to the mammal in any of a variety of manners known to persons skilled in the art, and may employ any of a variety of dosage forms.

EXAMPLE 3

Interaction of Valerian Root Extracts and Fractions of Valerian Root Extract with Human Dopamine D3 Receptors It has also been discovered, according to the present invention, that Valerian extracts demonstrate specificity for the Dopamine D3 subtype versus the other Dopamine receptors. Without being bound to a particular theory or action or functional hypothesis, it is believed that Mirapex (pramipexole), noted above, acts on the D3, D2, D4 receptor subtypes, and that Valerian's relative selectivity for the D3 subtype may be responsible for Valerian's lower incidence of side-effects relative to Mirapex.

TABLE 2

Effect of Valerian on ligand binding to human recombinant dopamine receptors. (The ligand used was $^3$H-SCH-23390 in the dopamine $D_1$ assay and $^3$H-Spiperone in all other assays.)

| Receptor | Assay # | N = | Conc. µg/mL | % Inhibition |
|---|---|---|---|---|
| Dopamine $D_1$ | 1 | 2 | 1000 | 36 |
|  | 1 | 2 | 100 | −8 |
|  | 1 | 2 | 10 | −2 |
|  | 2 | 3 | 1000 | 69 |
| Dopamine $D_{2L}$ | 1 | 2 | 1000 | 19 |
|  | 1 | 2 | 100 | 2 |
|  | 1 | 2 | 10 | −10 |
| Dopamine $D_{2S}$ | 1 | 2 | 1000 | 26 |
|  | 1 | 2 | 100 | −2 |
|  | 1 | 2 | 10 | 6 |
| Dopamine $D_3$ | 1 | 2 | 1000 | 77 |
|  | 1 | 2 | 100 | 13 |
|  | 1 | 2 | 10 | 6 |
|  | 2 | 4 | 2000 | 82 |
|  | 2 | 4 | 1000 | 49 |
|  | 2 | 4 | 500 | 24 |
|  | 2 | 4 | 250 | 17 |
|  | 2 | 4 | 125 | 6 |
|  | 2 | 4 | 62.5 | 7 |
|  | 2 | 4 | 31.25 | 4 |
| Dopamine $D_{4.2}$ | 1 | 2 | 1000 | 19 |
| Dopamine $D_{4.4}$ | 1 | 2 | 1000 | −15 |
|  | 1 | 2 | 100 | −8 |
|  | 1 | 2 | 10 | 10 |
| Dopamine $D_{4.7}$ | 1 | 2 | 1000 | 0 |

This example demonstrates the interaction of Valerian and fractions prepared from Valerian with human dopamine D3 receptors in vitro.

Low doses of dopamine D3 receptor agonists have been shown to increase slow wave sleep (SWS) and rapid eye movement (REM) sleep in animal models. Dopamine D3 agonists also reduce locomotor activity in rats. Studies indicate that treatment with a specific D3 agonist does not directly induce the release of dopamine. This suggests that the direct interaction of agonists with the dopamine D3 receptor is involved in the induction of sleep.

Aqueous and hydroalcoholic extracts of Valeriana officinalis L. (valerian) roots are commonly used as sedative agents. To understand the mechanism of this pharmacological activity, we investtigated the effect of Valerian on ligand binding to the human dopamine D3 receptor. Fractions prepared from such extracts were also tested for interaction with dopamine D3 receptors to identify individual compounds, or classes of compounds, that may be partially responsible for the sedative action of Valerian.

Figure 4:
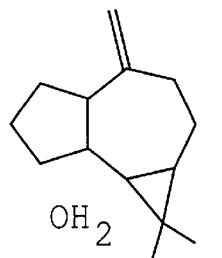
FIG. 4 illustrates the chemical structures of five structurally related compounds determined to be active in a dopamine D3 bio-assay according to the invention.
Figure 4:
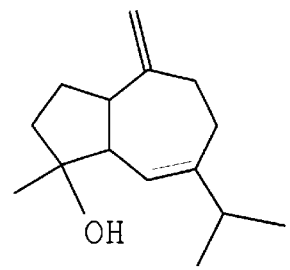
Figure 4:
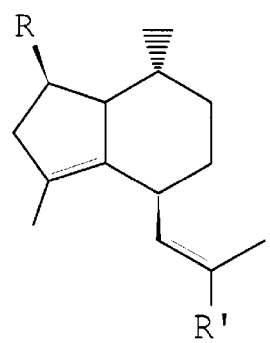
Figure 5A:
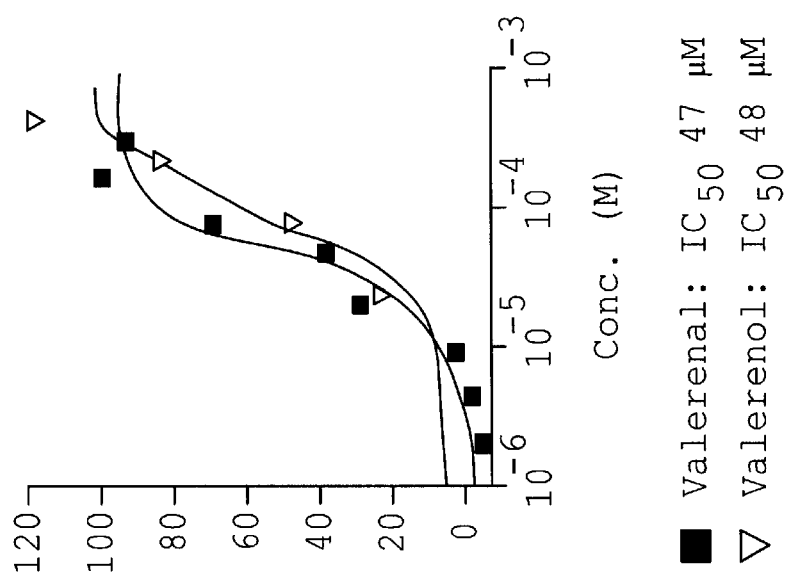
FIG. 5 illustrates the inhibition of ligand binding to the human dopamine receptor by various compounds isolated from Valerian according to the invention.
Figure 5B:
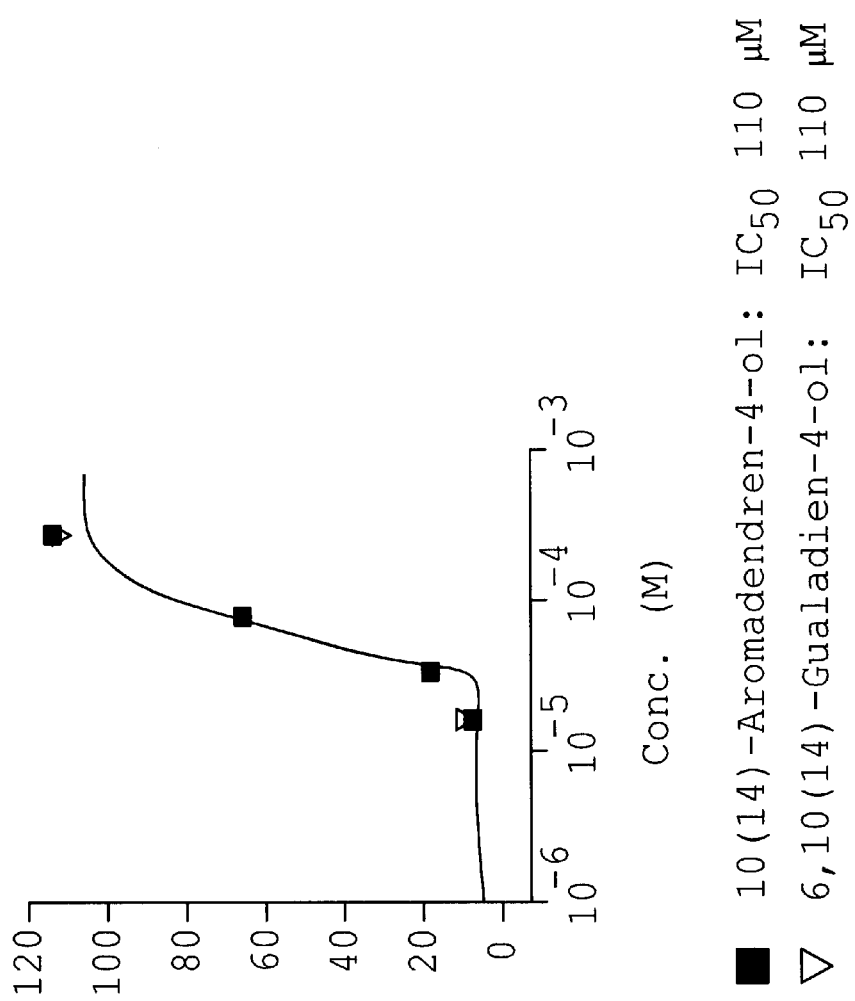
Figure 5C:
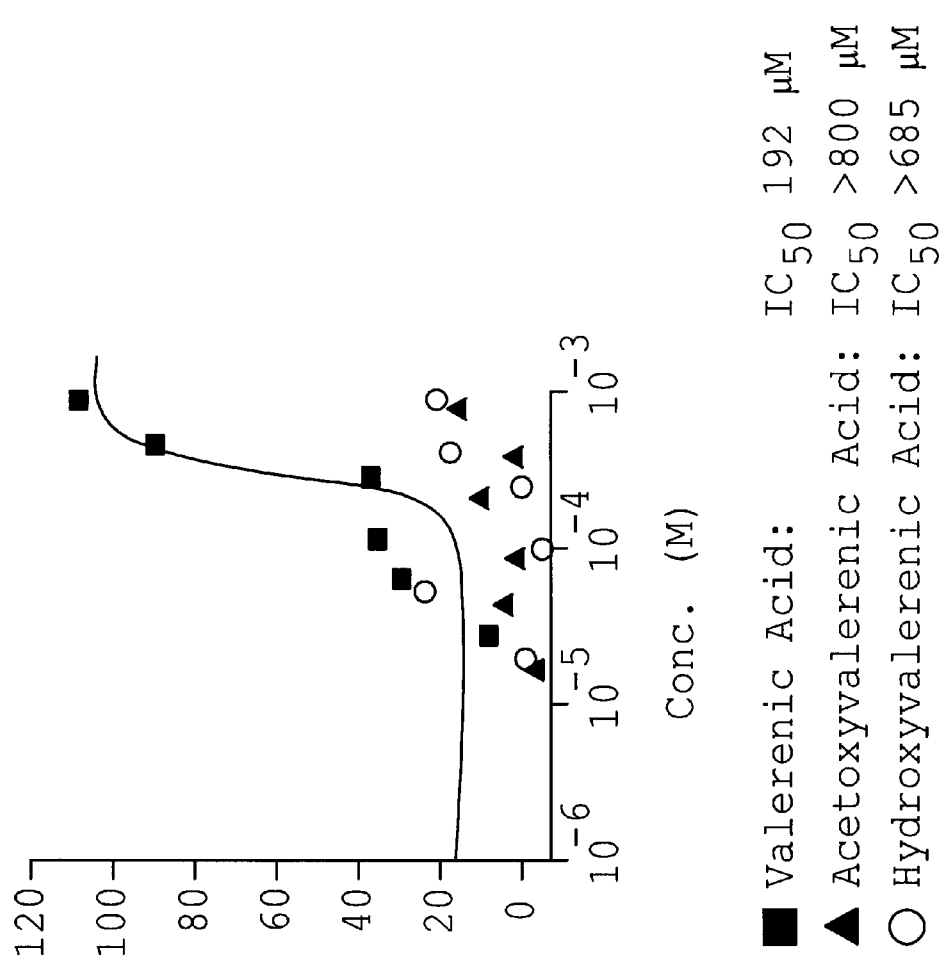

Materials and methods used in performing this example were as follows:

Valerian was subjected to the fractionation scheme schematically depicted in FIG. 4.

As the source of, and to isolate the receptors used in the example, membranes prepared from Chinese hamster ovarian (CHO) cells, stably transfected with a plasmid encoding the human dopamine D3 receptor, were used.

Sample preparation:

Stock solutions of the valerian root extract were prepared by dissolving in 50% ethanol/water followed by sonication and filtration (0.45 µm) or by dissolving in 100% DMSO. Valerian fractions were dissolved in 100% DMSO. Prior to analysis, stock solutions were diluted in appropriate buffer. In each assay, the final ethanol or DMSO concentration was less than or equal to 1%.

Receptor binding assays:

Standard receptor binding assays were performed at the following analytical laboratory: Panlabs Taiwan, Ltd., 158 Li-Teh Road, Peitou, Taipei, Taiwan, R.O.C. The assay method, based on the assay described in Sokoloff, P., Giros, B., Martres, M.-P., Bouthenet, M.-L. and Schwartz, J.-C. Molecular cloning and characterization of a novel dopamine receptor (D3) as a target for neuroleptics. Nature 347: 146–151, (1990), was as follows: The assay measures binding of [3H] Spiperone to human dopamine D3 receptors. CHO cells stably transfected with a plasmid encoding the human dopamine D3 receptor are used to prepare membranes in modified Tris-HCl pH 7.4 buffer using standard techniques. A 10 mg aliquot of membrane is incubated with 2 nM [$^3$H]-Spiperone for 120 minutes at 37° C. Non-specific binding is estimated in the presence of 25 µM S-(−)-sulpiride. Membranes are filtered and washed 3 times and the filters are counted to determine [$^3$H]-Spiperone specifically bound. Compounds are screened at 10 µM. Results were as follows: Kd=0.12 nM; Bmax=1.9 pmol/mg protein; Specific Binding=85%. The Reference Data were as depicted in the following table, Table 3:

TABLE 3

Reference Data For Recptor Binding Assay
Reference Data:

| Compound | IC$_{50}$ (nM) | Ki (nM) | nH |
|---|---|---|---|
| R-(−)-Apomorphine | 270 | 15 | 0.9 |
| (+)-Butaclamol | 13 | 0.73 | 1.0 |
| Chlorpromazine | 38 | 2.1 | 0.9 |
| Clozapine | 4,200 | 240 | 1.0 |
| Dopamine | 1,100 | 64 | 0.9 |
| cis-Flupenthixol | 0.83 | 0.047 | 0.9 |
| Haloperidol | 26 | 1.5 | 1.2 |
| SCH-23390 | >10,000 | — | — |
| SKF-38393 | >10,000 | — | — |
| *Spiperone | 0.7 | 0.04 | 1.0 |
| S-(−)-Sulpiride | 850 | 48 | 1.0 |

*Indicates standard reference agent used. SCH-23390=7-chloro-2,3,4,5-tetrahydro-3-methyl-5phenyl-1H-3-benzazepine-7ol; SKF-38393=2,3,4,5-tetrahydro-7,8-dihydroxy-1-phenyl-1H-3-benzazepine HCValerian root extract has been reported Valerian root extract has been reported to posses sedative activity, presumably through the interaction of one or more of its constituents with receptors mediating sedation. The neuromodulator, dopamine, is a suspected sleep-inducing factor through its specific interaction with dopamine receptors. While there are a number of known dopamine receptor subtypes, activation of the dopamine D3 receptor is most closely associated with dopamine's sleep-inducing and sedative effects. This has been demonstrated with agents that selectively activate the D3 receptor. Studies indicate D3 selective agonists induce both slow wave sleep (SWS) and rapid eye movement (REM) sleep in rats.

To understand Valerian's mechanism of action, Valerian was tested in this example for its ability to displace radio-labeled ligand ($^3$H-spiperone) from the human dopamine D3 receptor in vitro. The data from the testing of Valerian at various concentrations on different days is summarized below in Table 4. The results indicate that Valerian root extract interacts with dopamine D3 receptors in a concentration-dependent manner.

TABLE 4

Interaction of Valerian extract with Human Dopamine D3 Receptors

| Experiment No. | Concentration | N | % Inhibition |
|---|---|---|---|
| 1 | 1 µg/mL | 2 | 6 |
|  | 100 µg/mL | 2 | 13 |
|  | 1000 µg/mL | 2 | 77 |
| 2 | 31.3 µg/mL | 4 | 4 |
|  | 62.5 µg/mL | 4 | 7 |
|  | 125 µg/mL | 4 | 6 |
|  | 250 µg/mL | 4 | 17 |
|  | 500 µg/mL | 4 | 24 |
|  | 1000 µg/mL | 4 | 49 |
|  | 2000 µg/mL | 4 | 82 |
| 3 | 100 µg/mL | 2 | 24 |
|  | 500 µg/mL | 2 | 36 |

Figure 3:
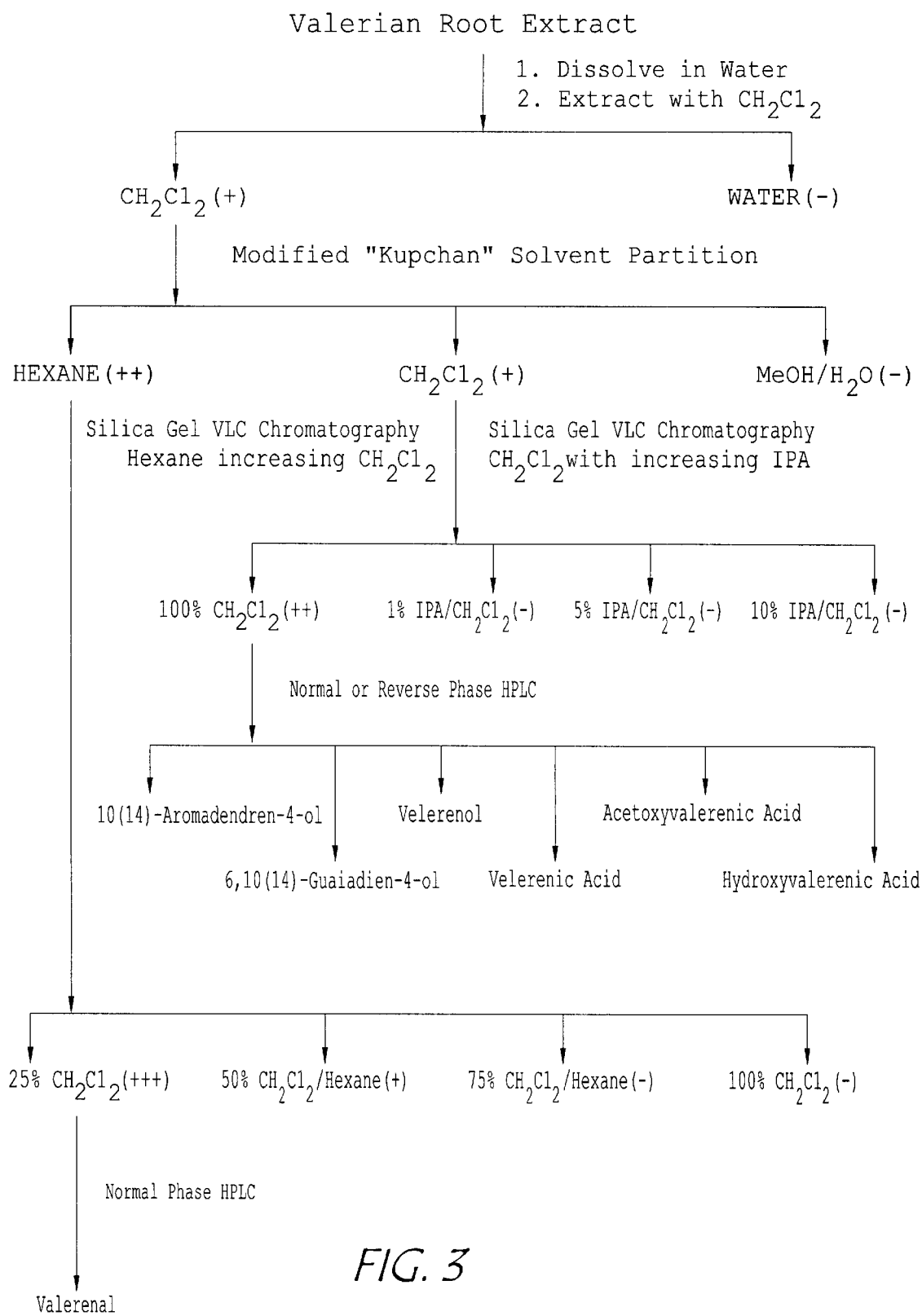
FIG. 3 illustrates a schematic Valerian fraction flow diagram including an exemplary isolation scheme used to assay dopamine D3 receptor binding activity.

In order to identify compounds or class of compounds from valerian root extract that interact with the dopamine D3 receptor, Valerian was subjected to bioactivity-guided fractionation (see FIG. 3). Valerian fractions were tested to determine their activity against the dopamine D3 receptor and active fractions were subjected to further sub-fractionation. The results from the testing of Valerian fractions and sub-fractions at various concentrations are summarized in Tables 5, 6, 7, and 8. These results indicate that several sub-fractions interact strongly with the receptor. Without being bound to any particular theory of action for the invention, the results of this example indicate that more than one compound may be responsible for the observed interaction of Valerian with the dopamine D3 receptor.

TABLE 5

Interaction of Valerian Fractions and Sub-fractions with Human Dopamine D3 Receptors

| Sample | Description | % Inhibition 500 µg/mL | 100 µg/mL |
|---|---|---|---|
| BKC-007-26-F0 | Valerian extract | 36 | 24 |
| BKC-007-26-F1 | CH$_2$Cl$_2$ soluble portion of BKC-007-26-F0 | 108 | 86 |
| BKC-007-26-F2 | Butanol soluble portion of BKC-007-26-F0 | 37 | 8 |
| BKC-007-26-F3 | Water soluble portion of BKC-007-26-F0 | -3 | 6 |
| BKC-007-26-F4 | Hexane soluble portion of BKC-007-26-F1 | 100 | 100 |
| BKC-007-26-F5 | CH$_2$Cl$_2$ soluble portion of BKC-007-26-F1 | 65 | 55 |
| BKC-007-26-F6 | Methanol soluble portion of BKC-007-26-F1 | 64 | -6 |
| BKC-007-26-F7 | Water elution of C18 column of BKC-007-26-F3 | 5 | -16 |
| BKC-007-26-F8 | Organic elution of C18 column of BKC-007-26-F3 | 11 | -20 |

TABLE 6

Interaction of Valerian Fractions and Sub-fractions with Human Dopamine D3 Receptors

| Sample | Description | % Inhibition 100 µg/mL | 20 µg/mL |
|---|---|---|---|
| KL-015-01-F1 | CH$_2$Cl$_2$ soluble portion of Valerian extract | 88 | 33 |
| KL-015-01-F4 | Hexane soluble portion of KL-015-01-F1 | 104 | 26 |
| KL-015-08-F1 | Silica Gel VLC fraction of KL-015-01-F4 | 79 | 36 |
| KL-015-08-F2 | Silica Gel VLC fraction of KL-015-01-F4 | 91 | 46 |
| KL-015-08-F3 | Silica Gel VLC fraction of KL-015-01-F4 | 89 | 42 |
| KL-015-08-F4 | Silica Gel VLC fraction of KL-015-01-F4 | 23 | 16 |
| KL-015-08-F5 | Silica Gel VLC fraction of KL-015-01-F4 | 5 | 19 |
| KL-015-08-F6 | Silica Gel VLC fraction of KL-015-01-F4 | -9 | 2 |
| KL-015-01-FS | CH$_2$Cl$_2$ soluble portion of KL-015-01-F1 | 76 | 30 |
| KL-015-03-F1 | Silica Gel VLC fraction of KL-015-01-F5 | 22 | 22 |
| KL-015-03-F2 | Silica Gel VLC fraction of KL-015-01-FS | 106 | 34 |
| KL-015-03-F3 | Silica Gel VLC fraction of KL-015-01-F5 | 113 | 42 |
| KL-015-03-F4 | Silica Gel VLC fraction of KL-015-01-FS | 102 | 54 |
| KL-015-03-F5 | Silica Gel VLC fraction of KL-015-01-F5 | 56 | 18 |

TABLE 7

Interaction of Valerian Sub-fractions with Human Dopamine D3 Receptors

| | | % Inhibition | | |
|---|---|---|---|---|
| Sample | Description | 100 µg/mL | 50 µg/mL | 25 µg/mL |
| KL-015-01-F4 | Hexane soluble portion of KL-015-01-F1 | ND | 58 | 22 |
| KL-015-10-F1 | Silica Gel Column Fraction of KL-015-03-F2 | 122 | 74 | 49 |
| KL-015-14-F3 | Silica Gel Column Fraction of KL-015-08-F1 | 126 | 92 | 85 |
| KL-015-19-F1 | Silica Gel Column Sub-Fraction of Pooled Active Fractions from Previous Steps | 98 | 56 | 51 |
| KL-015-19-F2 | Silica Gel Column Sub-Fraction of Pooled Active Fractions from Previous Steps | 19 | 14 | 13 |
| KL-015-19-F3 | Silica Gel Column Sub-Fraction of Pooled Active Fractions from Previous Steps | 70 | 55 | 31 |
| KL-015-19-F4 | Silica Gel Column Sub-Fraction of Pooled Active Fractions from Previous Steps | 86 | 44 | 22 |
| KL-015-19-FS | Silica Gel Column Sub-Fraction of Pooled Active Fractions from Previous Steps | 98 | 52 | 30 |
| KL-015-19-F6 | Silica Gel Column Sub-Fraction of Pooled Active Fractions from Previous Steps | 88 | 53 | 41 |
| KL-015-19-F7 | Silica Gel Column Sub-Fraction of Pooled Active Fractions from Previous Steps | 60 | 43 | 29 |
| KL-015-19-F8 | Silica Gel Column Sub-Fraction of Pooled Active Fractions from Previous Steps | 48 | 22 | 24 |
| KL-015-039-F2 | Preparatory TLC Fraction of Pooled Active Fractions from Previous Steps | 116 | 107 | 55 |

In summary, with regard to this example, it has been shown that Valerian inhibits ligand binding to the dopamine D3 receptor in a concentration dependent manner. Furthermore, the results of the bioactivity-guided fractionation indicate that there are compounds, or classes of compounds, from Valerian root extract that strongly interact with the dopamine D3 receptor.

EXAMPLE 4

Binding Potency of Further Purified Sub-Fractions

Highly active sub-fractions were fuirther purified and tested for their binding potency against the human dopamine D3 receptor, as outlined in Example 3. After full chemical characterization, active compounds were evaluated, as in Example 3. The results are shown in Table 8.

TABLE 8

Inhibition of Ligand Binding to the Human Dopamine D3 Receptor by Various Valerian Constituents

| Sample | Description | N | Conc. (µg/mL) | % Inhibition | Approximate | $EC_{50}$ |
|---|---|---|---|---|---|---|
| KL-015-040-F1 | Acetoxyvalerenic Acid MW 292 | 2 | 200 | 16 | >200 µg/mL | >685 µM |
| | | 2 | 100 | 1 | | |
| | | 2 | 50 | 10 | | |
| | | 2 | 25 | 3 | | |
| | | 2 | 12.5 | 7 | | |
| | | 2 | 6.25 | 1 | | |
| KL-015-025-F2 | Hydroxyvalerenic Acid MW 250 | 2 | 200 | 19 | >200 µg/mL | >800 µM |
| | | 2 | 100 | 17 | | |
| | | 2 | 50 | 0 | | |
| | | 2 | 25 | −3 | | |
| | | 2 | 12.5 | 21 | | |
| | | 2 | 6.25 | 2 | | |
| KL-015-039-F1 | Valerenic Acid MW 234 | 2 | 200 | 109 | 45 µg/mL | 192 µM |
| | | 2 | 100 | 87 | | |
| | | 2 | 50 | 34 | | |
| | | 2 | 25 | 31 | | |
| | | 2 | 12.5 | 25 | | |
| | | 2 | 6.25 | 10 | | |
| VM-022-034-F1 | 10(14)-Aromadendren-4-ol MW 220 | 1 | 100 | 115 | 24.2 µg/mL | 110 µM |
| | | 1 | 33.3 | 66 | | |
| | | 1 | 11.1 | 15 | | |
| | | 1 | 3.7 | 4 | | |
| VM-022-034-F2 | 6,10(14)-Guaiadien-4-ol MW 220 | 1 | 100 | 114 | 24.1 µg/mL | 110 µM |
| | | 1 | 33.3 | 66 | | |
| | | 1 | 11.1 | 15 | | |
| | | 1 | 3.7 | 5 | | |
| VM-022-034-F4 | Valerenol MW 220 | 1 | 100 | 119 | 10.5 µg/mL | 48 µM |
| | | 1 | 33.3 | 88 | | |

TABLE 8-continued

Inhibition of Ligand Binding to the Human Dopamine D3 Receptor by Various Valerian Constituents

| Sample | Description | N | Conc. (μg/mL) | % Inhibition | Approximate EC$_{50}$ | |
|---|---|---|---|---|---|---|
|  |  | 1 | 11.1 | 45 |  |  |
|  |  | 1 | 3.7 | 25 |  |  |
| VM-022-022-F1 | Degraded Valerenal | 1 | 100 | 31 | >100 μg/mL | NA |
|  |  | 1 | 33.3 | 31 |  |  |
|  |  | 1 | 11.1 | 21 |  |  |
|  |  | 1 | 3.7 | 18 |  |  |
| VM-022-033-F1 | Valerenal (VAL) | 2 | 50 | 112 | 10.2 μg/mL | 47 μM |
|  | MW 218 | 2 | 25 | 94 |  |  |
|  |  | 2 | 12.5 | 49 |  |  |
|  |  | 2 | 6.25 | 26 |  |  |
|  |  | 2 | 3.13 | 25 |  |  |
|  |  | 2 | 1.56 | 7 |  |  |
|  |  | 2 | 0.78 | −8 |  |  |
|  |  | 2 | 0.39 | 10 |  |  |
| CB-001 | Volatile Oil (VO) | 1 | 100 | 104 | 19.5 μg/mL | NA |
|  |  | 1 | 33.3 | 55 |  |  |
|  |  | 1 | 11.1 | 32 |  |  |
|  |  | 1 | 3.7 | 21 |  |  |
| Combination | VA, AVA, VAL and VO | 1 | 100 | 77 | 30.2 μg/mL | NA |
|  | (3.4:0.7:1); i.e. their ratio normally found in | 1 | 33.3 | 59 |  |  |
|  | Valerian extracts | 1 | 11.1 | 13 |  |  |
|  |  | 1 | 3.7 | 18 |  |  |

The various articles and other references of the scientific and/or medical literature, and the U.S. and foreign patents and patent applications cited herein, including those listed below, are hereby incorporated by reference; each constitutes a part of the disclosure of this specification. Furthermore, while specific embodiments, working examples, and prophetic examples of the invention have been described in detail to illustrate the broad applicability and principles underlying the invention, it will be understood by those of skill in the art that the invention may be embodied otherwise without departing from such broad applicability and principles.

References:

Boucher M A Restless legs syndrome in home healthcare. *Home Healthc Nurse* August 1997; 15(8):551–6.

Fox G N Restless legs syndrome. *Am Fam Physician* January 1986; 33(1):147–52.

Grandjean P Restless legs syndrome—current aspects. *Schweiz Rundsch Med Prax* Apr. 30, 1997; 86(18):732–6.

Homyak M, Voderholzer U, Hohagen F, Berger M, Riemann D Magnesium therapy for periodic leg movements-related insomnia and restless legs syndrome: an open pilot study. *Sleep* Aug. 1, 1998; 21(5):501–5.

Jones H J, Derodra J K Restless legs syndrome—a review. *Eur J Vasc Endovasc Surg* December 1997; 14(6):430–2.

Joy M S Clonazepam: benzodiazepine therapy for the restless legs syndrome. *ANNA J* December 1997; 24(6):686–9.

Krueger B R Restless legs syndrome and periodic movements of sleep, *Mayo Clin Proc* July 1990; 65(7):999–1006.

O'Keeffe S T Restless legs syndrome. A review. *Arch Intern Med* Feb. 12, 1996; 156(3):243–8.

Silber N H Restless legs syndrome. *Mayo Clin Proc* March 1997; 72(3):261–4.

Trenkwalder C, Walters A S, Hening W Periodic limb movements and restless legs syndrome. *Neurol Clin* August 1996; 14(3):629–50.

Walters A S Toward a better definition of the restless legs syndrome. The International Restless Legs Syndrome Study Group. *Mov Disord September* 1995; 10(5):634–42.

Wetter T C, Pollmacher T Restless legs and periodic leg movements in sleep syndromes. *J Neurol* April 1997; 244(4 Suppl 1):S37–45.

Williams D C Periodic limb movements of sleep and the restless legs syndrome. *Va Med Q* 1996 Fall; 123(4):260–5.

What is claimed is:

1. A method for diminishing undesired limb movements in a host, the method comprising the step of:
    administering to the host a pharmaceutically effective amount of one or more compounds of Valeriana selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid and combinations thereof.

2. The method of claim 1, further comprising the step of identifying that the host suffers from undesired limb movements.

3. The method according to claim 1, wherein said host is a mammal.

4. The method according to claim 3, wherein said host is a selected from the group of canines, felines, and rodents.

5. The method according to claim 3, wherein said host is a human.

6. The method according to claim 3, wherein said host is a mouse.

7. The method of claim 1, wherein said undesired limb movements are at least partially involuntary.

8. The method of claim 1, wherein the pharmaceutically effective amount of the one or more compounds of Valeriana inhibits ligand binding to the dopamine D3 receptor of the host and the extent of the inhibition of ligand binding to the dopamine D3 receptor of the host is a function of the concentration of the pharmaceutically effective amount of the one or more compounds of Valeriana.

9. The method of claim 8, wherein said undesired limb movements are at least partially involuntary.

10. The method of claim 8, wherein said host is a mammal.

11. The method of claim 10, wherein said host is a selected from the group of canines, felines, and rodents.

12. The method of claim 10, wherein said host is a human.

13. The method of claim 12, wherein said undesired limb movements are at least partially involuntary.

14. The method of claim 1, wherein the pharmaceutically effective amount of one or more compounds of Valeriana inhibits ligand binding to a peripheral benzodiazepine receptor of the host to a greater extent than the pharmaceutically effective amount of the one or more compounds of Valeriana inhibits ligand binding to a central benzodiazepine receptor of the host.

15. The method of claim 14, wherein said undesired limb movements are at least partially involuntary.

16. The method of claim 14, wherein said host is a mammal.

17. The method of claim 16, wherein said host is a selected from the group of canines, felines, and rodents.

18. The method of claim 16, wherein said host is a human.

19. The method of claim 18, wherein said undesired limb movements are at least partially involuntary.

* * * * *

UNITED STATES PATENT AND TRADEMARK OFFICE
CERTIFICATE OF CORRECTION

PATENT NO.    : 6,346,283 B1
DATED         : February 12, 2002
INVENTOR(S)   : Hoffman et al.

It is certified that error appears in the above-identified patent and that said Letters Patent is hereby corrected as shown below:

Drawings,
Fig. 3, under "Normal or Reverse Phase HPLC," please change "Velerenol" to
-- Valerenol --; please change "Velerenic Acid" to -- Valerenic Acid. --

Column 22,
Line 54, after "said host is" please delete the word "a".

Column 23,
Line 5, after "said host is" please delete the word "a".

Column 24,
Line 8, after "said host is" please delete the word "a".

Signed and Sealed this

Second Day of July, 2002

Attest:

Attesting Officer

JAMES E. ROGAN
Director of the United States Patent and Trademark Office